United States Patent [19]

Milner et al.

[11] Patent Number: 4,955,398
[45] Date of Patent: Sep. 11, 1990

[54] RELATING TO THE MONITORING OF ROD-LIKE ARTICLES

[75] Inventors: John K. Milner, Horton; Roger B. Dagnall, Milford-on-Sea, both of England

[73] Assignee: British-American Tobacco Company Limited, London, England

[21] Appl. No.: 374,634

[22] Filed: May 4, 1982

[30] Foreign Application Priority Data

May 13, 1981 [GB] United Kingdom ............... 8114553

[51] Int. Cl.$^5$ ............................................ A24B 5/60
[52] U.S. Cl. .................................. 131/280; 131/904; 131/908; 73/37; 73/37.5; 73/37.8
[58] Field of Search ................. 131/280, 904; 73/37, 73/37.5, 37.8

[56] References Cited

U.S. PATENT DOCUMENTS 4,103,535  8/1978  Mutter et al. .................. 131/904

*Primary Examiner*—V. Millin
*Attorney, Agent, or Firm*—Kane, Dalsimer, Sullivan, Kurucz, Levy, Eisele and Richard

[57] ABSTRACT

The invention is based on the realization that for a rod-like article, a cigarette for example, having a plurality of ventilation gas flows, the flows can be equated to a single equivalent flow nominally occurring at an "equivalent ventilation point". By establishing one or more flow regimes in a rod-like article and measuring gas pressures, the articles can be monitored for displacement of the equivalent ventilation point, such displacement being indicative of the position of out-of-specification gas flows.

11 Claims, 4 Drawing Sheets

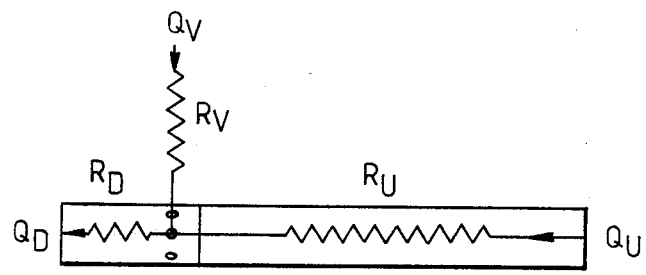
Fig. A
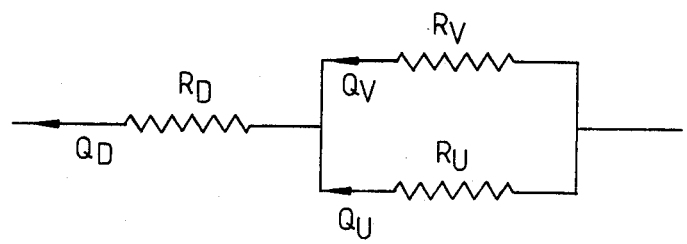
Fig. B
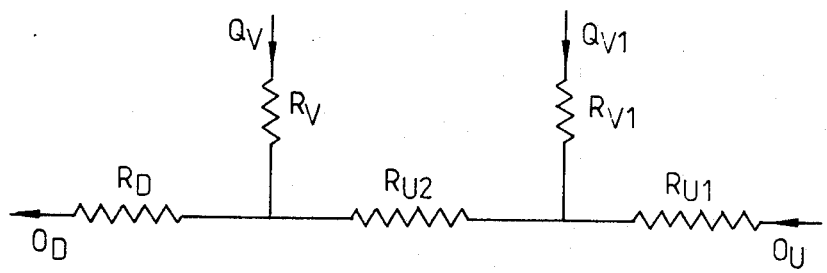
Fig. C

RELATING TO THE MONITORING OF ROD-LIKE ARTICLES

This invention relates to the monitoring of rod-like articles, cigarettes for example.

The ventilation value of a cigarette during smoking is defined as that proportion of the smoke/air mixture drawn from the mouth end of the cigarette which is represented by the air which has been drawn into the cigarette through the wrapping thereof. To permit ingress of ventilation air into the cigarette, the wrapping may be inherently air permeable and/or it may be provided with ventilation perforations. For the purposes of quality control in the manufacture of cigarettes a ventilation value is determined for unlit cigarettes. Apparatus may be employed which establishes an air flow through the length of an unlit cigarette in a direction towards the mouth end thereof and which permits measurement to be made of the flow rate ($Q_V$) of ventilation air to a sealed cavity extending around the cigarette wrapper and of the flow rate ($Q_D$) of air from the mouth end of the cigarette. The ventilation value (V) is then $Q_V/Q_D$.

The air flows into and out of a ventilated cigarette may be represented in relation to an electrical analogy. In the cigarette illustrated in FIG. A of the accompanying drawings it is assumed that the only ventilation air flow is one which occurs through a ring of perforations extending around a tipping wrapper. In FIG. A, $R_U$ is the resistance to air flow represented by the tobacco rod and that portion of the filter disposed upstream of the ventilation perforations. The resistance to air flow of that portion of the filter disposed downstream of the ventilation perforations is designated $R_D$, and the resistance to air flow of the ventilation perforations and, if it is present, of underlying air permeable plugwrap, is designated $R_V$.

Since the air flows $Q_U$ and $Q_V$ are both from ambient atmosphere, the resistances $R_U$ and $R_V$ can be represented as being connected in parallel. The electrical analogy circuit is thus of the form illustrated in FIG. B.

From this circuit it may be established that ventilation (V) may be expressed in terms of resistances, as:

$$\frac{R_U}{R_V + R_U}$$

It may be noted that ventilation is independent of the downstream resistance ($R_D$).

If in a filter cigarette in addition to a ventilation flow ($Q_V$) into the filter, there is a flow ($Q_{V1}$) into the tobacco rod, the electrical analogy circuit will be as shown in FIG. C.

The flow ($Q_{V1}$) may occur as a result of the cigarette paper having been deliberately perforated or because it possesses a degree of inherent air permeability and/or because of a fault condition in the cigarette paper such as a tear or hole therein or a portion of the lap seam not having been sealed.

In that both of the flows $Q_V$ and $Q_{V1}$ are from atmosphere, the resistances $R_V$, $R_{V1}$ and $R_{U2}$ can be considered to be connected in a delta network. Thus by application of a delta-star transformation the electrical analogy circuit takes the form shown in FIG. D, which can be represented in a simpler form as per FIG. E. In FIG. E, $R_{UE}$, $R_{DE}$ and $R_{VE}$ designate the upstream, downstream and ventilation equivalent resistances respectively.

The increased ventilation value is given as $$V = \frac{R_{UE}}{R_{VE} + R_{UE}}$$

As will be appreciated, the equivalent ventilation flow ($Q_{VE}$) is the sum of the filter and cigarette rod ventilation flows, i.e. $Q_V + Q_{V1}$. The equivalent ventilation flow may be considered as nominally occurring at the point of juncture of the upstream and downstream equivalent resistances, which point may be designated the "equivalent ventilation point" (EVP).

As will also be appreciated, a single equivalent flow could be determined if the additional flow occurred through the filter wrapping, whether to one side or the other of the ring of ventilation perforations. Indeed, the principle is of general application and can be applied to a smoking article having any number of modes of ventilation through the smoking article wrapping, in that any number of contributory ventilation flows occurring at various respective positions along the length of a smoking article can be equated to a single equivalent flow nominally occurring at an equivalent ventilation point. Furthermore, it is the case that any cigarette is fully defined as far as its pneumatic characteristics are concerned when each of $R_{UE}$, $R_{DE}$ and $R_{VE}$ are determined.

Whereas the determination of ventilation values for unlit cigarettes by the direct measurement of the values of $Q_V$ and $Q_D$ is practicable as a laboratory procedure, it is not so easily carried out by means of on-line apparatus installed on a high speed cigarette making unit to monitor each finished cigarette. A number of proposals have been made for the on-line monitoring of ventilation. According to these various proposals, ventilation values are established indirectly, usually by making pressure rather than flow measurements.

One method of determination of a ventilation value of an unlit cigarette by way of the measurement of air pressures involves the application at the end of the cigarette remote from the mouth end of an air-flow inducing pressure of known magnitude, while the mouth end is in sealed contact with a pressure measuring device. The applied pressure causes a flow of air through the cigarette wrapping. If the cigarette is a filter tipped cigarette and the filter is ventilated, the air flow may be substantially wholly through ventilation perforations in a tipping wrapper. The ventilation value may be obtained from the relationship $$V = \frac{P_1 - P_2}{P_1}$$

where:
$P_1$ is the applied pressure and
$P_2$ is the pressure indicated by the pressure measuring device.

The determination of ventilation by applying an airflow inducing pressure of value $P_1$ at the end of a cigarette remote from the mouth end and measuring the value $P_2$ of the pressure at the closed mouth end still applies when there are a plurality of ventilation flows through the wrapping. However, whether in such on-line monitoring of cigarette ventilation or in the direct laboratory procedure there is detected a change in ventilation indicative of a change in one or more of the ventilation flows or of a cigarette construction fault, the ventilation value of itself gives no indication of which flow or flows has changed or of the position of the fault along the cigarette length.

It is an object of the present invention to provide means of monitoring smoking articles and other rod-like articles which enables position indicative information relating to the equivalent ventilation flow to be obtained. The present invention is based on the realisation of the above mentioned concept of an equivalent ventilation point.

The present invention provides a method of monitoring a succession of rod-like articles, wherein one or more flow regimes is/are established in each rod-like article in order to determine the relationship which the upstream and downstream equivalent gas flow resistances of the article bear to each other, and detection is made of variations in the relationship indicative of the position of out-of-specification gas flows.

If the relationship which the upstream and downstream equivalent resistances of a rod-like article bear to each other differs from a specified target value by more than a preset limit amount, the rod-like article in question may be designated a reject, in which case it may be directed to a reject path.

If the rod-like articles are cigarettes, they may be plain or filter tipped cigarettes. The inventive method is also applicable to the monitoring of filter rod lengths.

Out-of-specification gas flows in cigarettes may occur because, for example, wrapping of incorrect air permeability is used or because of the malfunctioning of on-machine wrapping perforating apparatus. Other reasons include holes or tears in the wrapping and the non-sealing of a wrapping seam. The position of the equivalent ventilation point of a cigarette may be shifted longitudinally thereof by the occurrence of any such fault condition. Yet further faults which may affect the position of the equivalent ventilation point are those which cause changes in filter and/or tobacco rod gas flow resistance.

The method according to the invention may comprise a procedure wherein in the case of each article there is closed, or substantially closed, to gas flow the ventilation equivalent resistance ($R_{VE}$) or, in turn, the upstream equivalent resistance ($R_{UE}$) and the downstream equivalent resistance ($R_{DE}$) and a gas flow is established through the other two resistances in series to obtain pressure values to each side of each of the upstream and downstream equivalent resistances.

The method according to the invention may comprise another procedure in one flow regime of which there is closed, or substantially closed, to gas flow the upstream or the downstream equivalent resistance and a gas flow, of determined flow rate, is established through the other of the upstream and downstream resistances and the equivalent ventilation resistance in series to obtain pressure values to each side of each of the two series resistances. In a second flow regime of this procedure a gas flow, of determined flow rate, is established by applying to the article at one end thereof a gas-flow inducing pressure with all three of the equivalent resistances being open to gas flow. The pressure difference between the ends of the article is determined while this latter gas flow is maintained.

The method according to the invention may comprise a further procedure in first and second flow regimes of which gas flows are established in respect of each article by applying to the article at first and second ends respectively a gas-flow inducing pressure with all three of the equivalent resistances being open to gas flow and determining for each flow regime the ventilation flow rate and the flow rate through one at least of the upstream and downstream resistances.

If it may be safely assumed that the gas-flow resistance per unit length of the article of the material within the wrapping is substantially constant, it may be necessary to determine the value of one only of the upstream and downstream resistances in order to provide position indicative information relating to the equivalent ventilation flow. The single value may be determined by the establishment of only one flow regime.

In order that the invention may be clearly understood and readily carried into effect reference will now be made, by way of example, to FIGS. 1-6 of the accompanying drawings, of which:

Figure 1:
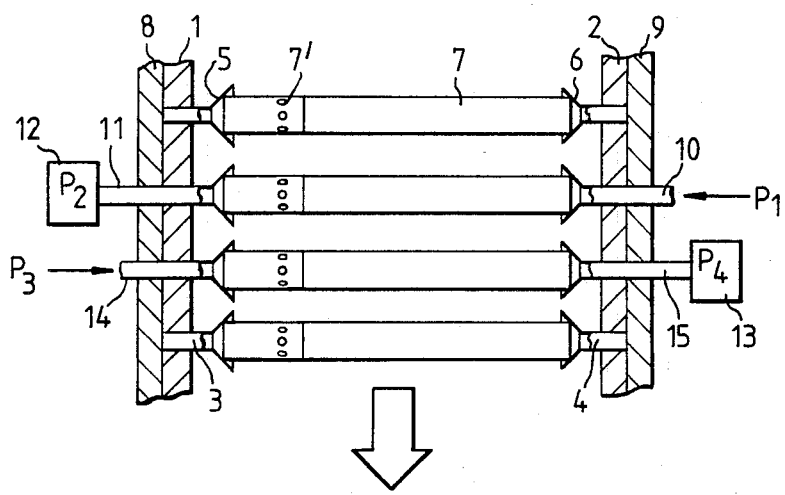
FIG. 1 shows, diagrammatically, parts of a drum, and associated parts, of a cigarette monitoring apparatus.

In FIG. 1 reference numerals 1 and 2 designate end rings of a fluted drum, being part of, for example, a cigarette tipping attachment machine. Gas-flow passages 3, 4 extend through the rings 1, 2 in line with each flute of the drum. At the inner ends of the passages 3, 4 seals 5, 6 are provided. When cigarettes 7 are disposed in the flutes the ends of the cigarettes are in substantially air-tight contact with the seals 5, 6. Outwardly disposed of the rings 1, 2 of the drum are stationary rings 8, 9, which are in sealing contact with the respective drum end rings 1, 2.

Extending through the stationary ring 9 is a duct 10 and, at an axially aligned location thereto, a duct 11 extends through the stationary ring 8 from a pressure measuring cell 12. As may be seen from FIG. 1, as the fluted drum rotates, in the direction indicated by the broad arrow, each cigarette in turn arrives at a position in which the cell 12 is put into communication with the duct 10 via a passage 4, the interior of the cigarette, a passage 3 and the duct 11. Such position is termed the first test station.

Further rotation of the fluted drum brings each cigarette in turn to a second test station in which a second pressure measuring cell 13 is put into communication with a duct 14 which extends through the stationary ring 8. The cell 13 and the duct 14 intercommunicate via passages 3, 4, the interior of the cigarette and a duct 15 which extends through the stationary ring 9 to the cell 13.

Figure 2:
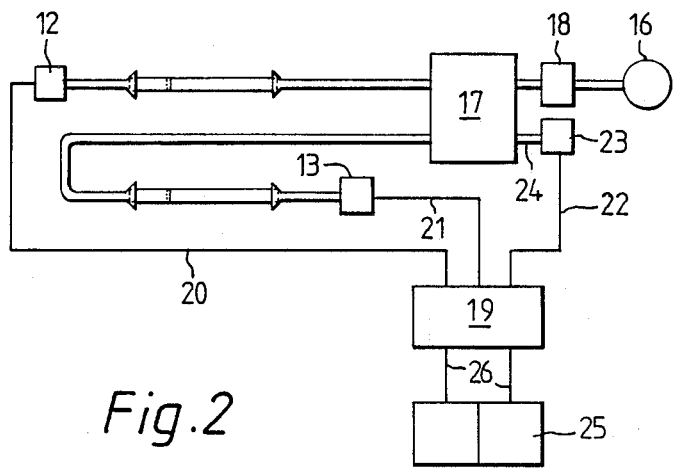
FIG. 2 shows a schematic of the cigarette monitoring apparatus of FIG. 1.

Referring to FIG. 2, air under pressure may be supplied from a source 16 to a plenum chamber 17 via a pressure regulator 18. The above mentioned ducts 10 and 14 communicate, at their ends remote from the stationary rings 9 and 8 respectively, with the chamber 17.

A microprocessor 19 is arranged to receive electrical signals from the pressure measuring cells 12, 13 via leads 20, 21 respectively, and via a lead 22 from a further pressure measuring cell 23 which communicates with the chamber 17 via a short duct 24. The microprocessor 19 is connected to a display unit 25 by leads 26.

In operation of the cigarette monitoring apparatus, when a cigarette arrives at the first test station air at a pressure $P_1$ is applied to the interior of the cigarette via the duct 10 and a passage 4. Air flows from the cigarette through the wrapping thereof. In the case of the cigarettes shown in FIG. 1, air flows through a row of filter ventilation perforations 7'. An electrical signal indicative of the air pressure $P_2$ obtaining at the mouth end of the filter passes from the cell 12 to the microprocessor 19 via the lead 20.

By closing the mouth end of the cigarette to air flow, the downstream equivalent resistance ($R_{DE}$) is closed to air flow and air flows through the upstream equivalent resistance ($R_{UE}$) and the ventilation equivalent resistance ($R_{VE}$) in series.

When the cigarette subsequently arrives at the second test station air at pressure $P_3$ is applied at the filter end of the cigarette via the duct 14 and a passage 3. An electrical signal indicative of the air pressure $P_4$ obtaining at the distal end of the tobacco rod passes from the cell 13 to the microprocessor 19 via the lead 21.

By closing the distal end of the tobacco rod to air flow, the upstream equivalent resistance ($R_{UE}$) is closed to air flow and air flows through the downstream equivalent resistance ($R_{DE}$) and the ventilation equivalent resistance ($R_{VE}$) in series.

In the microprocessor 19 a calculation is made of ventilation value V, as $$\frac{P_1 - P_2}{P_1}$$

In order to obtain positional information on the equivalent ventilation flow the microprocessor is also programmed to carry out a calculation of the ratio of the downstream to upstream equivalent resistances. This is obtained by $$\frac{R_{DE}}{R_{UE}} = \frac{P_2(P_3 - P_4)}{P_4(P_1 - P_2)}$$

The equivalent ventilation point calculated from the $R_{DE}/R_{UE}$ ratio would be at the position of the ring of ventilation perforations 7' if no other ventilation flow occurred through the cigarette wrapping. It is though usual for the cigarette paper, i.e. that portion of the wrapping surrounding the tobacco rod, to possess a degree of air permeability. In such case, because of the additional ventilation flow through the cigarette paper, the equivalent ventilation point will be located to that side of the ring of perforations 7' further from the mouth end of the filter.

Values of ventilation and $R_{DE}/R_{UE}$ are displayed by the display unit 25. If the longitudinal or circumferential sealing of the wrapping is faulty or if tipping or cigarette paper is faulty or of other than the specified permeability, not only will the detected ventilation deviate from the correct value, but the $R_{DE}/R_{UE}$ ratio will so change as to provide information indicative of the position of the source of the out-of-specification ventilation condition.

Figure 3:
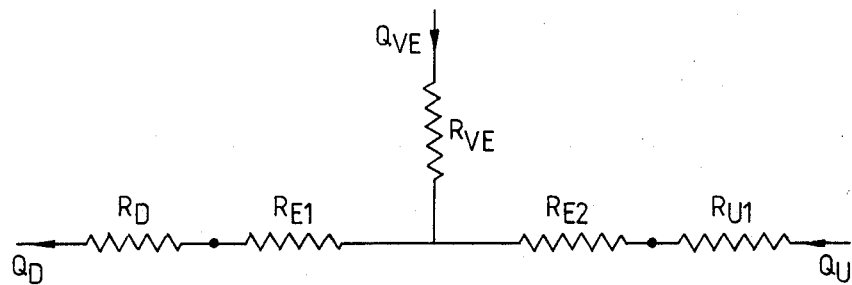
FIGS. 3-5 show, diagrammatically, respective variations of the cigarette monitoring apparatus of FIGS. 1 and 2.
Figure 3:
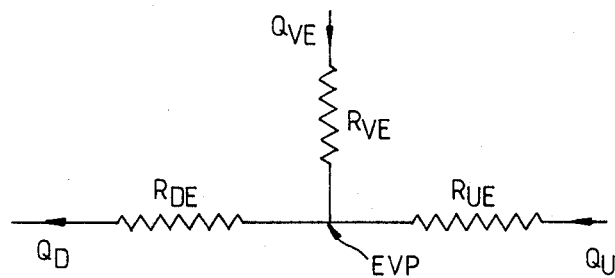
Figure 3:
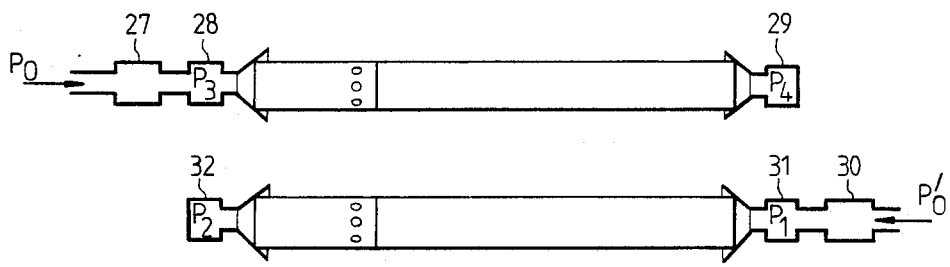
Figure 4:
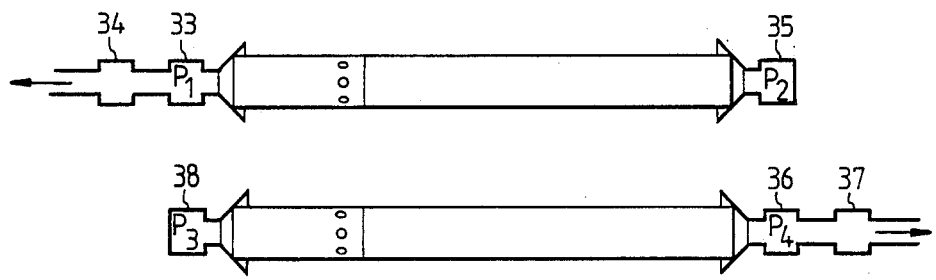
Figure 5:
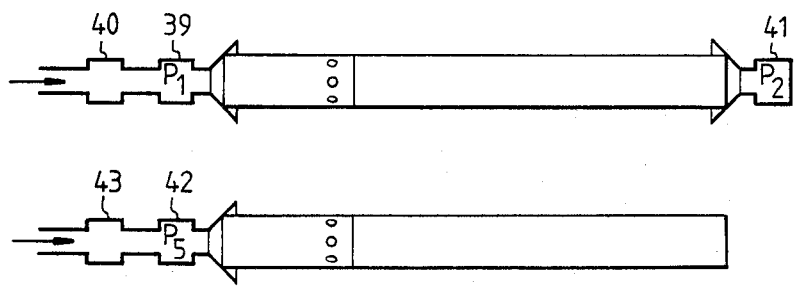

Variations of the cigarette monitoring apparatus of FIGS. 1 and 2 are diagrammatically illustrated in FIGS. 3, 4 and 5. In each case the apparatus operates on a two station principle and provides signals from which, by way of a microprocessor, information about the upstream and downstream equivalent resistances of cigarettes may be obtained, although as is mentioned below, in some cases limited but possibly valuable information may be derived from a single one of the stations.

At the first test station of the apparatus of FIG. 3 air under pressure is fed to a cigarette, at the filter end thereof, via a resistor 27 and a pressure measuring cell 28, the other end of the cigarette being closed by a pressure measuring cell 29. At the second test station air is fed to the other end of the cigarette via a resistor 30 and a pressure measuring cell 31, the filter end of the cigarette being closed by a pressure measuring cell 32. The upstream, downstream and ventilation equivalent resistances can then be calculated from the following relationships.

$$R_{DE} = \frac{P_3 - P_4}{P_0 - P_3} \cdot R$$

$$R_{UE} = \frac{P_1 - P_2}{P_0' - P_1} \cdot R'$$

$$R_{VE} = \frac{P_4 \cdot R}{P_0 - P_3} \text{ or } \frac{P_2 \cdot R'}{P_0' - P_1}$$

where
$P_0$ and $P_0'$ are the applied pressures,
$P_1 P_2$, $P_3$ and $P_4$ are the respective pressures at the cells 31, 32, 28 and 29, and
R and R' are the respective resistances established by the resistors 27 and 30.

The ventilation value may be determined from the relationship $$V = \frac{P_1 - P_2}{P_1}$$

If it may be assumed that the air-flow resistance value of the tobacco rods of the cigarettes being monitored remains substantially constant from cigarette to cigarette, position indicative information relating to the equivalent ventilation flow may be obtained by resorting only to the test procedure at the second station, from which procedure values of $R_{UE}$, $R_{VE}$ and V are obtainable.

At the first test station of the apparatus of FIG. 4 a pressure below ambient is applied at the filter end of the cigarette, through a flow rate control device 34, so as to induce an air flow, of known flow rate Q, from the cigarette through a pressure measuring cell 33. The other end of the cigarette is closed by a pressure measuring cell 35. At the second test station air is drawn, at a known flow rate Q', from the other end of the cigarette via a pressure measuring cell 36 and a flow rate control device 37, the filter end of the cigarette being closed by a pressure measuring cell 38. The upstream, downstream and ventilation equivalent resistances can then be calculated from the following relationships.

$$R_{DE} = \frac{P_2 - P_1}{Q}$$

$$R_{UE} = \frac{P_3 - P_4}{Q'}$$

$$R_{VE} = \frac{P_2}{Q} \text{ or } \frac{P_3}{Q'}$$

where
P₁, P₂, P₃ and P₄ are the respective pressures at the cells 33, 35, 38 and 36.

The ventilation value may be determined from the relationship.

$$V = \frac{P_4 - P_3}{P_3}$$

Again, if only the second test station procedure is carried out calculation of $R_{UE}$, $R_{VE}$ and V can be made and this may be useful if the above referred to assumption is valid.

At both the first and the second test stations of the cigarette monitoring apparatus of FIG. 5 there is applied an air flow to the mouth end of the filter of the test cigarette. At the first station the air passes, at a known flow rate Q, through a pressure measuring cell 39 and a flow rate control device 40, the other end of the cigarette being closed by a pressure measuring cell 41. At the second test station an air flow is applied to the mouth end of the filter, at a known flow rate Q', first through a flow rate control device 43 and then through a pressure measuring cell 42, but in this case the other end of the cigarette is open to ambient atmosphere.

The upstream and downstream equivalent resistances can then be calculated from the following relationships.

$$R_{DE} = \frac{P_1 - P_2}{Q}$$

$$R_{UE} = \frac{P_2}{Q}\left[\frac{P_5Q - (P_1 - P_2)Q'}{P_1Q' - P_5Q}\right]$$

$$R_{VE} = \frac{P_2}{Q}$$

where
P₁, P₂ and P₅ are the respective pressures at the cells 39, 41 and 42.

The ventilation value may be determined from the relationship $$V = \frac{P_5Q - (P_1 - P_2)Q'}{P_2Q'}$$

Figure 6:
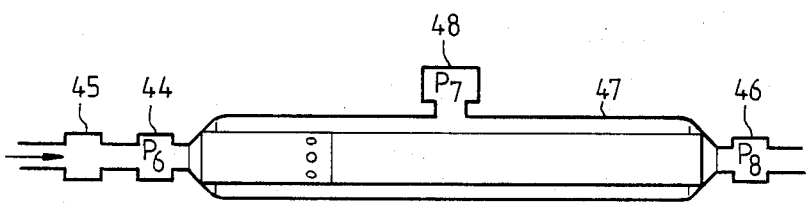
FIG. 6 shows, diagrammatically, a single station cigarette monitoring apparatus.

The cigarette monitoring apparatus of FIG. 6 operates on a one station principle to provide data sufficient for the determination of both the upstream and the downstream equivalent resistances of the cigarettes. In addition to cigarette end seals, the apparatus of FIG. 6 comprises housing means 47 which serves to sealingly house the peripheral surface of a cigarette. A pressure measuring cell 48 communicates with the interior of the enclosure means 47. In operation of the apparatus air under pressure is fed to a cigarette through a flow rate control device 45 and a pressure measuring cell 44. Air flows through the length of the cigarette, at flow rate Q, and outwardly therefrom via a pressure measuring device 46. The ventilation equivalent resistance is closed to air flow. The upstream and downstream equivalent resistances can then be calculated from the following relationships.

$$R_{DE} = \frac{P_6 - P_7}{Q}$$

-continued $$R_{UE} = \frac{P_7 - P_8}{Q}$$

where
P₆, P₇ and P₈ are the respective pressures at the cells 44, 48 and 46.

It may be noted that P₇ is the pressure obtaining at the E.V.P.

It is also possible to determine the $R_{DE}/R_{UE}$ ratio by using the known laboratory ventilation apparatus which is operable to draw air from the mouth end of a cigarette and to provide measurements of the flow rate ($Q_V$) of ventilation air and the flow rate ($Q_D$) of air from the mouth end. The ventilation (V) is then given as $Q_V/Q_D$. The $R_{DE}/R_{UE}$ ratio can be determined by means of the simple expedient of taking a ventilation measurement (V') with the cigarette entered into the ventilation apparatus in what heretofore for a filter tipped cigarette would have been considered to be the wrong way round. In other words the cigarette is so disposed in the ventilation apparatus that air is drawn from the tobacco end rather than the filter end of the cigarette. This "reverse" ventilation (V') is given as $Q'_V/Q'_U$—where $Q'_U$ is the air flow rate from the tobacco rod. The $R_{DE}/R_{UE}$ ratio is then given as $$\frac{V'(1 - V)}{V(1 - V')}$$

The $R_{DE}/R_{UE}$ ratio is also given as $$\frac{Q_U \cdot Q'_V}{Q'_D \cdot Q_V}$$

where
$Q_U$ is the flow rate of air drawn into the tobacco end of the cigarette during the determination of ventilation (V), and
$Q'_D$ is the flow rate of air drawn into the mouth end of the cigarette during the determination of reverse ventilation (V').

Those skilled in the art of cigarette ventilation testing will readily recognise variations in the above described procedures whereby air flows are in directions opposite to those above indicated and also that an air flow in a given direction may be forced or induced.

EXAMPLE

Cigarettes were made up each having a tobacco rod of a length of 64 mm, wrapped in cigarette paper of relatively low porosity, and a cellulose acetate filter of a length of 20 mm. The respective air-flow resistances of the tobacco rod and the filter were such that, with an air-flow at a rate of 17.5 cc/min., the resultant pressure drops were 80 and 40 mm water gauge.

The filters each comprised a porous plugwrap and a tipping was used to connect the filter to the tobacco rod, which tipping had been electrostatically perforated over a 5 mm width band. The distance from the mouth end of the filter to the marging of the band nearest thereto was 10 mm.

Using a ventilation test apparatus it was found that the $R_{DE}/R_{UE}$ ratio of the cigarettes was 0.356.

$$\therefore R_{DE} = \frac{0.356 \times 120}{1.356 \times 17.5} = \frac{31.5}{17.5}$$

and the equivalent ventilation point is $$\frac{31.5}{17.5} \times \frac{17.5 \times 20}{40} = 16 \text{ mm from the mouth end of the filter.}$$

Thus the equivalent ventilation point was 1 mm upstream of the perforated ventilation zone. This indicates that some ventilation flow occurred through the cigarette paper.

The cigarettes were then each perforated at the midpoint of the tobacco rod in order to simulate damage to the cigarette paper or unintentional use of cigarette paper of a higher permeability value.

The $R_{DE}/R_{UE}$ ratio was then found to be 0.785, which means that the equivalent ventilation point had moved to a location about 30 mm from the mouth end of the filter.

We claim:

1. A method of monitoring a succession of rod-like articles, wherein one or more flow regimes is established in each rod-like article in order to determine the relationship which the upstream and downstream equivalent gas flow resistances of the article bear to each other, and detection is made of variations in the relationship indicative of the position of out-of-specification gas flows.

2. A method according to claim 1, wherein if said relationship for one of said articles differs from a target value of said relationship by more than a limit amount, said one of said articles is directed to a reject path.

3. A method according to claim 1 or 2, wherein a gas flow is established through each rod-like article from one end to the other end thereof with the ventilation equivalent resistance being closed, or substantially closed, to gas flow, and determination is made of the gas pressures obtained at the upstream and downstream ends of the rod-like article and at the equivalent ventilation point.

4. A method according to claim 1 or 2, wherein one end of each rod-like article is closed, or substantially closed, to gas flow, a gas-flow inducing pressure is established at the other end of the article, and determination is made of the gas pressures obtaining at the respective ends of the rod-like article.

5. A method according to claim 4, wherein each rod-like article is subjected to a further flow regime in which said other end of the rod-like article is closed, or substantially closed, to gas flow, with said one end of the article being open to gas flow, a gas-flow inducing pressure is established at said one end of the article, and determination is made of the gas pressures obtained at the respective ends of the rod-like article.

6. A method according to claim 4, wherein with said one end of each rod-like article being open, or substantially open, to gas flow, a gas-flow inducing pressure is established at the other end of the article and determination is made of the gas pressure obtained at the said other end.

7. A method according to claim 1 or 2, wherein according to one flow regime one end of each rod-like article is open, or substantially open, to gas flow, a gas-flow inducing pressure is established at the other end of the article, and determination is made of the gas flow rate obtained at said other end of the article and of the gas flow rate through the ventilation equivalent resistance, and according to another flow regime said other end of the article is open, or substantially open, to gas flow, a gas-flow inducing pressure is established at the said one end of the article, and determination is made of the gas flow rate obtained at the said one end of the article and of the gas flow rate through the ventilation equivalent resistance.

8. A method according to claims 1 or 2, wherein each of the said rod-like articles is a filter tipped cigarette.

9. Rod-like article monitoring apparatus comprising conveying means operable to convey a succession of rod-like articles to a test station, seal means whereby a first end of a rod-like article at the station may be closed, or substantially closed, to gas flow and whereby the other, second end of the rod-like article may be connected to a gas flow passage, gas-flow inducing means operable to establish a gas-flow inducing pressure in said passage, and gas pressure measuring means by way of which the respective pressures obtained at the first and second ends of the article may be determined.

10. Apparatus according to claim 9, wherein said conveying means is operable to convey said succession of rod-like articles to a further test station, and said apparatus comprises means enabling determination to be made of the respective gas pressures obtained at the first and second ends of an article at said further test station with the second end of the article being closed, or substantially closed, to gas flow and a gas flow being induced across the first end of the article.

11. Rod-like article monitoring apparatus comprising seal means whereby a first end of a rod-like article may be connected to a gas flow passage, housing means operable to sealingly house the peripheral surface of the rod-like article over substantially the whole length thereof, gas-flow inducing means operable to establish a gas-flow inducing pressure in said passage, and gas pressure measuring means by way of which the pressures difference obtained between the first and second ends of the article and the pressure obtained within said housing may be determined.

* * * * *